Figure 1:
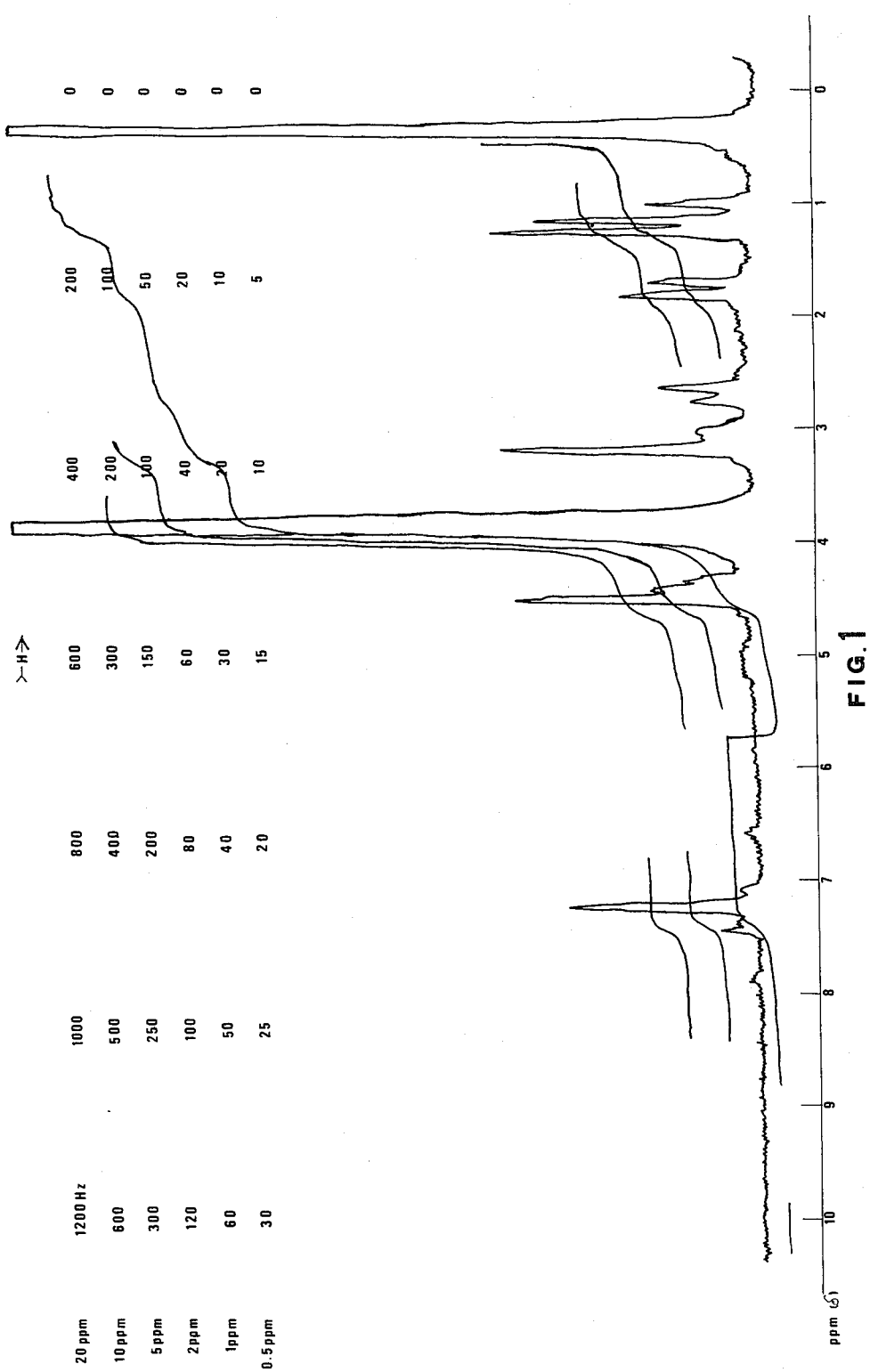

United States Patent [19]

Ferruti et al.

[11] 4,367,176

[45] Jan. 4, 1983

[54] ESTERS OF ARYLPROPIONIC ACIDS ENDOWED WITH AN ANTI-INFLAMMATORY ACTIVITY AND RELATED PHARMACEUTICAL COMPOSITIONS

[75] Inventors: Paolo Ferruti; Ferdinando Danusso, both of Milan; Maria C. Tanzi, Monza; Giuseppe Quadro, Milan, all of Italy

[73] Assignee: Ausonia Farmaceutici s.r.l., Pomezia, Italy

[21] Appl. No.: 233,658

[22] Filed: Feb. 11, 1981

[30] Foreign Application Priority Data

Feb. 13, 1980 [IT] Italy .............................. 19878 A/80

[51] Int. Cl.$^3$ .............................................. C07C 69/76
[52] U.S. Cl. .................................... 548/482; 549/70; 560/51; 560/52; 560/56; 560/100; 560/112; 424/283; 424/308

[58] Field of Search ................... 560/51, 100, 112, 52, 560/56; 260/326.1; 549/70; 424/283, 308

[56] References Cited

FOREIGN PATENT DOCUMENTS 1195488  6/1970  United Kingdom ................ 560/112

*Primary Examiner*—Paul J. Killos
*Attorney, Agent, or Firm*—Bucknam and Archer

[57] ABSTRACT

The present invention concerns diesters of polyethylene glycols (with n ranging between 4 approximately and 100 approximately) with 2-arylpropionic acids (known as anti-inflammatory agents). These esters, while possessing all the characteristics of low toxicity and gastric injuring effects shown by the related acids, differ advantageously from the latter because their anti-inflammatory activity is much more prolonged, and their bio-availability markedly better.

14 Claims, 2 Drawing Figures

ESTERS OF ARYLPROPIONIC ACIDS ENDOWED WITH AN ANTI-INFLAMMATORY ACTIVITY AND RELATED PHARMACEUTICAL COMPOSITIONS

DESCRIPTION OF THE INVENTION

The present invention concerns new esters of arylpropionic acids, characterized by the general formula (I)

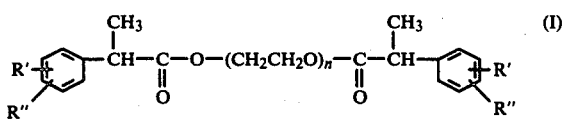

where n represents a number ranging between 4 approximately and 100 approximately while R' may be a hydrogen atom (in which case R" represents the isobutyl, benzoyl, 2-thenoyl or 1-oxo-2-isoindolinyl residue) or R' may be a phenyl group (in which case R" represents a fluorine atom or still R' and R" represents together a benzene ring orthocondensated on the first ring, and carrying a methoxyl group. R' and R", preferably, are such as that (I) represents diesters of polyethylene glycols with the 2-(4-isobutyl-phenyl)-, 2-[4-(2-thenoyl)-phenyl]-, 2-[4-(1-oxo-2-isoindolinyl)phenyl]-, 2-(3-benzoyl-phenyl)-, 2-(3-fluoro-4-phenyl-phenyl)- and 2-(6-methoxy-2-naphthyl)-propionic acids that are all known for their anti-inflammatory properties. Preferably, moreover, n takes mean values ranging between 10 approximately and 50 approximately. The present invention, moreover, also concerns the enantiomers of the esters characterized by the formula (I).

The compounds (I), comparable to the corresponding acids with respect to their properties of low toxicity and gastric injuring effects, present with an anti-inflammatory activity that, although showing an equivalent intensity, differs markedly for a more prolonged duration. This evidence constitutes a considerable advantage since the corresponding acids are generally characterized by a short-term action. Also pharmacokinetic investigations show a bioavailability markedly higher, even of a 100 percent rate, than that shown by the corresponding acids. Therefore, a further object of the present invention is represented by pharmaceutical compositions endowed with an anti-inflammatory activity, containing as active ingredient at least one ester of formula (I), in the form of a racemic or of enantiomers.

An additional object of the present invention is represented by a procedure for the preparation of the esters (I), that consists in reacting the compounds of formula (II)

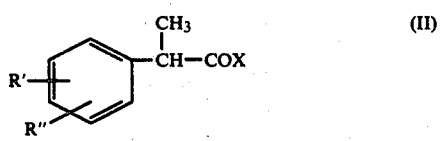

where R' and R" have the above stated significance while X represents either a hydroxyl group or preferably an activating group such an alkoxyl, Cl, 1-imidazolyl group or still a residue apt to form, with the remaining moiety of the molecule, an anhydride function), with a polyethylene glycol, characterized by the formula $HO-(CH_2CH_2O)_n-H$, where n has the above stated significance, preferably ranging (as mean value) between 10 approximately and 50 approximately. Preferably, the compounds (II) are brought into reaction with polyethylene glycols in a molar ratio of 2:1 approximately, preferably around 2.5:1, in order to ensure the maximum diester yield.

The below reported example duly illustrates the invention, constituting however no limitation to its scope.

EXAMPLE 1

Diester of 2-(4-isobutyl-phenyl)propionic acid with polyethylene glycol 1000 (n=20, 3 in the mean)

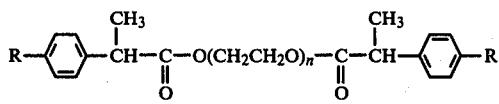

where R=isobutyl; n=20.3 (in the mean).

21 grams (0.102 moles) of 2-(4-isobutyl-phenyl) propionic acid (ibuprofen) are dissolved in 300 ml of anhydrous $CHCl_3$. The resulting solution is added with 21 g of carbonyl-diimidazole (CDI, 0.13 moles) under agitation, at room temperature. As soon as the effervescence is terminated (half-an-hour approximately), the reaction mixture is added with 40 g of polyethylene glycol 1000 (0.4 moles) previously dried under vacuum at 30° C. and dissolved in 200 ml of anhydrous $CHCl_3$. The reaction is caused to occur in a thermostatized bath at 60° C. for 48 hours. The excess of ibuprofen results to be 25 percent approximately with respect to the quantity required for the formation of the diester.

The resulting solution is washed two times with 100 ml of water, two times with 100 ml of 0.1 N HCl, two further times with 100 ml of water, still two times with 100 ml of 0.1 N NaOH, and finally three times with 100 ml of water.

After drying on $Na_2SO_4$, the solution is filtered and concentrated under vacuum. The concentrated solution is shaken with anhydrous n-heptane (about 1000 ml); n-heptane is then decanted, and anhydrous ethyl ether (500 ml approximately) is added cooling down to 0°–5° C. in order to reduce to a minimum the solubility of the diester.

After further decantation, the product is dried under vacuum (0.1 mm Hg). The product solidifies, taking a waxy consistance, only after elimination of any trace of solvent. Yield 40 g (73 percent).

On the basis of the NMR spectrum (FIG. 1) the overall rate of esterification results to correspond to 25 percent in weight of ibuprofen that can be liberated. This datum proves comparable with the one provided by the indirect titration (theoretical: 1.67 meq.; practical: 1.525 meq., equivalent to 27.3 percent of ibuprofen that can be liberated); moreover, the direct titration indicates the absence of unbound ibuprofen.

The resulting product (that for brevity's sake shall be from now on called by the code name MR-654) is scarcely soluble in water, in aliphatic hydrocarbons and in diethylether, soluble in methanol, ethanol and acetone. Its TLC characteristics shall be reported further on.

EXAMPLE 2

Diester of 2-(4-isobutyl-phenyl) propionic acid with polyethylene glycol 2000 (n=43.04 in the mean)

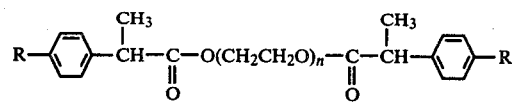

where R=isobutyl; n=43.04 (in the mean).

An analogously as in Example 1, 11 g of ibuprofen (0.053 moles) are dissolved in 150 ml of anhydrous $CHCl_3$. The resulting solution is added to 11 g of CDI (0.068 moles), under agitation a room temperature.

As soon as the effervescence is terminated (half-an-hour approximately), the reaction mixture is added to 40 g of polyethylene glycol 2000 (0.02 moles), previously dried under vacuum at 30° C., dissolved in 200 ml of anhydrous $CHCl_3$. The excess of ibuprofen results to be 33 percent approximately with respect to the disubstitution of polyethylene glycol 2000. The reaction is caused to occur in a thermostatized bath at 68° C. for 48 hours. The chloroform solution is washed two times with 100 ml of water, two times with 100 ml of 0.1 N HCl, two further times with 100 ml of water, still two times with 100 ml of 0.1 N NaOH, and finally three times with 100 ml of water. After drying on $Na_2SO_4$, the resulting solution is filtered and concentrated under vacuum. The product is precipitated by addition, to the concentrated solution, of 1 liter of a 2:1 n-heptane/ether mixture (anhydrous solvents). The precipitate is filtered by pump and dried under vacuum (0.1 mmHg). Yield 42 g (88 percent).

Figure 2:
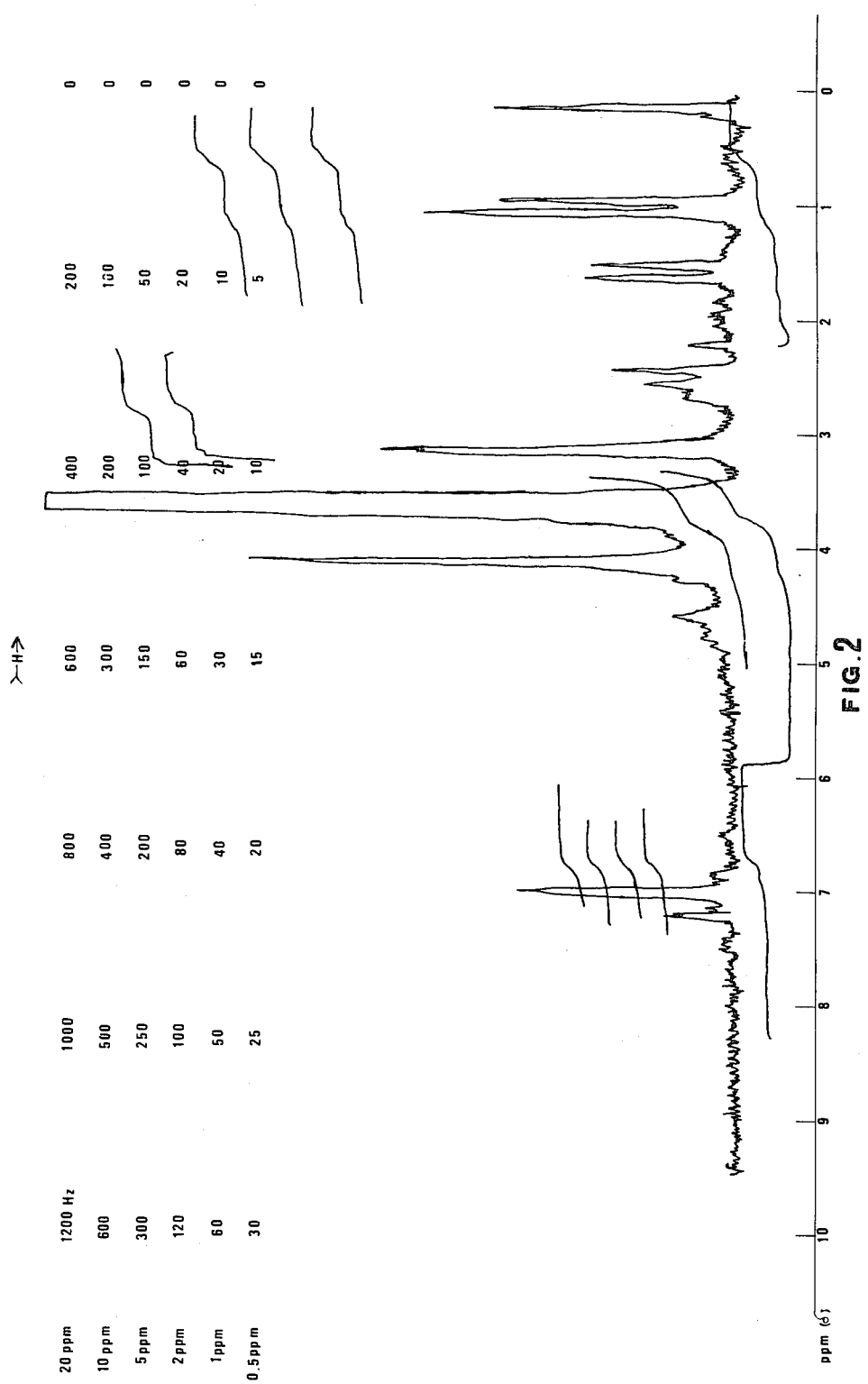

On the basis of the NMR spectrum (FIG. 2) the overall esterification rate results to correspond to 15 percent approximately, in weight, of Ibuprofen that can be liberated. This datum coincides with the datum resulting from the indirect titration (theoretical: 0.85 meq.; practical: 0.75 meq.); moreover the direct titration proves the absence of unbound ibuprofen.

The resulting product (that, for brevity's sake shall be defined from now on with the code name MR-655) is scarcely soluble in aliphatic hydrocarbons and in diethylether, soluble in water, alcohols and acetone.

The diesters MR-654 and MR-655 were subjected to chromatography on Merck 60 Kieselgel plates; the elution was carried out with a $MeOH/CHCl_3$/glacial AcOH in a 70:35:4 ratio.

Iburprofen, polyglycols and diesters present with the following coefficients of retention:

| | $R_f$ |
|---|---|
| MR-654 | 0.68 |
| MR-655 | 0.47 |
| Ibuprofen | 0.78 |
| PEG 1000 | 0.4 |
| PEG 2000 | 0.32 |

The spots, pertaining to the two oligomeric derivatives (I) are single. TLC does not reveal in any case the presence of unbound ibuprofen. The replication of the preparations of the products MR-654 and MR-655 allowed to remark their reproducibility.

The pharmacotoxicologic properties of the diesters (I) are hereinbelow described on the basis of the examples provided by the compounds MR-654 and MR-655.

ACUTE TOXICITY

The acute toxicity of the two products, established orally in the mouse, provided LD 50 values higher than 2000 mg/kg. Also the gastric injuring effects of MR-654 and MR-655 result to be very low, ie mildly lower than those induced by ibuprofen.

ANTI-INFLAMMATORY ACTIVITY

The anti-inflammatory activity of MR-654 and MR-655 was assessed in comparison with that of ibuprofen, at equimolar doses, by the carrageenin edema test in the rat (Wistar male and female animals, body weight of 160–200 g; twelve animals for each compound and for each experiment). 1 percent carrageenin in saline was injected, at the dosage rate of 0.1 ml, subcutaneously, into the plantar area of the left paw. Ibuprofen was given at doses of 100 mg/kg/os (in 5 percent gum arabic); MR-654 and MR-655 were given in doses equivalent to 100 mg/kg/os of ibuprofen, ie of 370 and 625 mg/kg/os.

The products were administered 1, 3 and 6 hours respectively before the carrageenin injection; the values were always read 4 hours after the injection of carrageenin assessing the percent swelling of the paw versus the value observed at the time 0 (carrageenin inocula).

The results were expressed in terms of percent protection considering the swelling, observed in the control group, as equal to 100.

The protection exerted by the investigational compounds is expressed in the attached Table 1, which enables to remark that the anti-inflammatory action of MR-654 and MR-655 is exerted acccording to a typical slow release effect.

TABLE 1

Percent protection from the carrageenin edema after oral administration, in the rat, of ibuprofen, MR-654 and MR-655, control groups being made equal to 100

| Product | Detection after hours | | | | |
|---|---|---|---|---|---|
| | 1 | 2 | 3 | 4 | 6 |
| Ibuprofen | 60 | 44 | 28 | 24 | 20 |
| MR-654 | 45 | 49 | 54 | 45 | 27 |
| MR-655 | 50 | 42 | 26 | 24 | 32 |

Actually, the activity of ibuprofen results to be much higher than that exerted by the other two compounds at the first hour; but, already starting from the second hour, the new related values can be considered almost comparable.

From third hour on, a quite different pattern is observed, ie:

the activity of ibuprofen decreases markedly and constantly;

MR-654 attains in these detections a maximum peak of efficacy that results to be prolonged in the course of time keeping, despite a dropping parabola, values always markedly higher than those provided by ibuprofen;

in case of MR-655, progressively from the third hour, the line of activity increases gradually and markedly through an evident delayed release.

PHARMACOKINETICS

The plasma pharmacokinetics of MR-654 and MR-655 was investigated following oral administration in the albino rat, Wistar strain, male sex, bodyweight ranging between 180 and 220 grams. Since these compounds liberate ibuprofen into the body, the kinetics of said latter drug was also investigated at the doses of 58.8 mg/kg and 19.2 mg/kg.

peak (and therefore a longer half-life) and can therefore be considered as long-acting ibuprofen.

TABLE 2

Plasma concentrations and standard deviations (mcg/ml) of ibuprofen in the male rat, after intraperitoneal and oral administration of MR-654, and oral administration of MR-655

| Product | Dose given mg/kg | hour of administration | | | | |
|---|---|---|---|---|---|---|
| | | 0.5 | 1 | 2 | 5 | 7 |
| Ibuprofen os | 19.2 | | 26.2 ± 9.7 | 10.5 ± 1.9 | 0.12 ± 0.03 | |
| Ibuprofen i.p. | 58.8 | 215.2 ± 33.4 | 104.7 ± 12.4 | 18.3 ± 11.0 | | 6.2 ± 2.4 |
| Ibuprofen os | 58.8 | | 71.7 ± 23.6 | 34.2 ± 7.7 | 12.1 ± 2.2 | 9.1 ± 1.5 |
| MR 654 os | 120(*) | | 116.1 ± 11.7 | 39.3 ± 14.2 | 12.9 ± 3.5 | 10.7 ± 3.0 |
| MR 655 os | 120(**) | | 13.4 ± 2.1 | 10.9 ± 2.7 | 7.5 ± 0.3 | 7.2 ± 0.4 |

(*)correspondent to 38.8 mg of ibuprofen
(**)correspondent to 19.2 mg of ibuprofen In the case of ibuprofen, the plasma kinetics was also investigated after oral administration to the purpose of being provided with an assessment of the rate of intestinal absorption of this drug.

The investigational compounds were given by oral gavage, suspended in 0.5 percent gum arabic; an analogous suspension was also used in the case of the intraperitoneal administration. Blood withdrawals from the animals were made from a sublingual vein, according to the procedure described by Ferro Milone M. and Barbiera P. (Atti della Soc.It.Sicenze Veterinarie, 1974, 28, 394).

The plasma determination of ibuprofen was carried out by a gas chromatographic method according to the procedure described by Runci F. M. and Segre G. (Recent Development in Chromatrography and Electrophoresis, A. Frigerio, L. Renoz Eds., Elsevier, Amsterdam, 1979, page 199).

Table 2 shows the plasma kinetic patterns after oral and intraperitoneal administration of 58.8 mg/kg, and after oral administration of 19.2 mg/kg. The intraperitoneal kinetics, provided that it can be assimilated to the intravenous kinetics, can be expressed by the following biexponential equation:

$$X(t) = 468\ e^{-2.1t} + 32\ e^{-0.23t}$$

where X=concentration as mcg/ml and t=hours

The half-life, calculated on the basis of the second component, results to be equivalent to 3 hours approximately.

The areas under the curve (AUC) are in a first approximation (for times up to the 7th hour) equivalent to 190 (os) and 325 (ip), in a ratio equivalent to a 60 percent level.

The kinetic patterns of MR-654 and MR-655 are shown in Table 2; the content of ibuprofen of the two molecules is such that the used dose of MR-654, equivalent to 120 mg/kg, corresponds to 38.8 mg/kg of ibuprofen while the dose of MR-655, equivalent to 19.2 mg/kg, corresponds to 19.2 mg/kg of ibuprofen.

On the basis of said content of ibuprofen, the plasma curves were compared with the curves resulting from the administration of 58.8 and 19.2 mg/kg of ibuprofen. In the case of MR-654 the comparison was also made with said two doses of ibuprofen since the plasma kinetics of ibuprofen had not been investigated at the dose of 38.8 mg/kg. A line going through the peaks (at the first hour) of the plasma levels of ibuprofen at the two tested doses (58.8 and 19.2 mg/kg) was plotted in order to better assess the kinetic patterns. It could be stated on the basis of said line that MR-654 and MR-655 present with a slower drop of the plasma concentration after the

We claim:
1. Esters of arylpropionic acids characterized by the general formula (I)

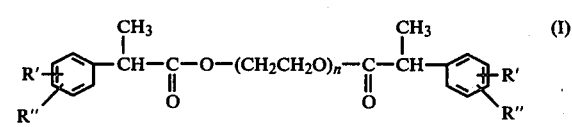

wherein n is a number ranging between 10 approximately and 50 and (a) R' is hydrogen, R" is isobutyl, benzoyl, 2-thenoyl or 1-oxo-2-isoindolinyl residue or (b) R' is a phenyl group, R" is fluorine or (c) R' and R" form together a benzene ring orthocondensated on the first ring, and carrying a methoxyl group as well as their enantiomers.

2. The compound according to claim 1 which is the diester of 2-(4-isobutyl-phenyl) propionic acid with polyethylene glycol 1000 and n=20.3 in the mean.

3. The compound according to claim 1 which is the diester of 2-(4-isobutyl-phenyl) propionic acid with polyethylene glycol 2000 and n=43.04 in the mean.

4. The compound according to claim 1 which is the diester of 2-[4-(2-thenoyl)phenyl] propionic acid with polyethylene glycol 1000 and n=20.3 in the mean.

5. The compound according to claim 1 which is the diester of 2-[4-(2-thenoyl)] phenyl propionic acid with polyethylene glycol 2000 and n=43.04 in the mean.

6. The compound according to claim 1 which is the diester of 2-[4-(1-oxo-2-isoindolinyl)phenyl] propionic acid with polyethylene glycol 1000 and n=20.3 in the mean.

7. The compound according to claim 1 which is the diester of 2-[4-(1-oxo-2-isoindolinyl)phenyl] propionic acid with polyethylene glycol 2000 and n=43.04 in the mean.

8. The compound according to claim 1 which is the diester of 2-(3-benzoyl-phenyl) propionic acid with polyethylene glycol 1000 and n=20.3 in the mean.

9. The compound according to claim 1 which is the diester of 2-(3-benzoyl-phenyl) propionic acid with polyethylene glycol 2000 and n=43.04 in the mean.

10. The compound according to claim 1 which is the diester of 2-(3-fluoro-4-phenyl) propionic acid with polyethylene glycol 1000 and n=20.3 in the mean.

11. The compound accordiing to claim 1 which is the diester of 2-(3-fluoro-4-phenyl) propionic acid with polyethylene glycol 2000 and n=43.04 in the mean.

12. The compound according to claim 1 which is the diester of 2-(6-methoxy-2-naphthyl) propionic acid with polyethylene glycol 1000 and n=20.3 in the mean.

13. The compound according claim 1 which is the diester of 2-(6-methoxy-2-naphthyl) propionic acid with polyethylene glycol 2000 and n=43.04 in the mean.

14. A pharmaceutical composition endowed with an anti-inflammatory and analgesic activity, which contains as the active ingredient at least one ester of an arylpropionic acid of general formula (I)

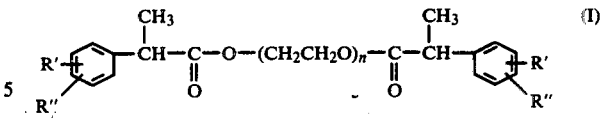

wherein n is a number ranging between 10 approximately and 50 and (a) R' is hydrogen, R" is isobutyl, benzoyl, 2-thenoyl or 1-oxo-2-isoindolinyl residue or (b) R' is a phenyl group, R" is fluorine or (c) R' and R" form together a benzene ring orthocondensated on the first ring, and carrying a methoxyl group as well as their enantiomers.

* * * * *